United States Patent [19]

Goebel

[11] 4,144,450  
[45] Mar. 13, 1979

[54] X-RAY POWDER DIFFRACTOMETER

[75] Inventor: Herbert Goebel, Graefelfing, Fed. Rep. of Germany

[73] Assignee: Siemens Aktiengesellschaft, Berlin & Munich, Fed. Rep. of Germany

[21] Appl. No.: 818,086

[22] Filed: Jul. 22, 1977

[30] Foreign Application Priority Data

Aug. 23, 1976 [DE] Fed. Rep. of Germany ....... 2637945

[51] Int. Cl.² ............................................ G01N 23/20
[52] U.S. Cl. ..................................... 250/272; 250/274
[58] Field of Search ......................... 250/272, 273, 274

[56] References Cited

U.S. PATENT DOCUMENTS

| 3,934,134 | 1/1976 | Bens | 250/272 |
| 4,076,981 | 2/1978 | Sparks | 250/272 |

Primary Examiner—Craig E. Church
Attorney, Agent, or Firm—Hill, Gross, Simpson, Van Santen, Steadman, Chiara & Simpson

[57] ABSTRACT

An X-ray powder diffractometer and associated computing system is disclosed for diffraction analysis of samples by the generation of an intensity diagram. A detector having a position sensitive element is advanced along an arc over a desired angle by a step motor. A control circuit connected to the step motor produces impulses corresponding to advancement of the step motor. These impulses are continually summed as an indication of the current position of the detector along the arc. The position sensitive element in the detector produces position signals corresponding to the position at which the detected X-rays strike the element. These position signals are digitallized. The position address is added to the sum of the impulses from the step motor control means to produce a composite sum which is indicative of the precise angle at a given moment at which an X-ray photon is detected by the sensitive element in the detector. As the detector moves along the arc, the composite sum is continually updated. By these means all X-rays falling successively into a certain diffraction angle are accumulated in the same channel of a multichannel analyzer independent of the movement of the position sensitive detector along the arc.

4 Claims, 2 Drawing Figures

X-RAY POWDER DIFFRACTOMETER

BACKGROUND OF THE INVENTION

1. Field of the Invention

The invention concerns an X-ray powder diffractometer having a source for producing a monochromatic X-ray beam and a detector with position-sensitive behavior for carrying out intensity diagram plots of the positional disperson of the X-ray beam in Bragg-Brentano, Guinier, or Seeman-Bohlin analyses of fine crystalline materials.

2. Description of the Prior Art

X-ray particle diffractometers of the kind described herein are known and are used for diffractometer processes according to Bragg-Brentano, Guinier, Seemann-Bohlin and others like them. Such an X-ray powder diffractometer is described, for example, in Fundamentals and Application of X-ray Fine Structure Analysis, Hans Neff, Oldenburg Publishing House, 1959, particularly at page 200.

With such diffractometers, radiographic analyses are carried out on fine crystalline materials. In principle FIG. 1 illustrates a known arrangement for the Bragg-Brentano process of diffraction analysis. The X-ray beam, which emanates from a source 1 for monochromatic X-ray transmission, passes through an aperture stop 2 and strikes sample 3. This sample 3 provides a pattern which is analyzed through an angle $\theta$. The beam 4, which has been deflected by the sample, has focusing areas which lie on an arc 5 according to the angle of deflection. It is common practice to record the intensity which occurs in the region of the aperture stop 7 and which is dependent on angle $\theta$ in order to produce and intensity distribution. A detector 6 is employed which is sensitive to position and which is illustrated with a line and provided with aperture stop 7 adjacent thereto. It is also common practice to arrange the receiving surface of detector 6 as indicated by the line in the figure. This orientation of the receiving surface of detector 6 deviates from arc 5 for the position of sharp focusing, this deviation being reasonable, however, when a sufficiently close aperture stop 7 is employed. This deviation has as its purpose the arrangement of detector 6 in a simpler manner in the mechanism. In addition it is necessary in order to properly establish the position sensitive behavior of detector 6 that the deflected X-ray beam 4 be received as perpendicular as possible relative to the receiving surface of detector 6.

From the prior art it is known to record the so-called powder diagram point-by-point through the given angle $\theta$ with the detector 6 on the measured arc 8. This recording requires considerable expenditure of time in order to cover the entire angle $\theta$ along arc 8 point-by-point, as is normal practice, where a sector angle of approximately 160° is to be covered.

In order to cover this sector of the measured arc 8, the detector 6 is shifted step-wise by given angle increments in which case it is essential that the angle at which detector 6 is set each time is as precise as possible so that different powder recordings can be combined with each other. A precise setting of the prescribed angular position requires a correspondingly precise mechanical construction and a suitable guidance system. Particular difficulties occur if the step-wise thrust occurs especially quickly to permit the total recording of the powder diagram to be carried out as quickly as possible over the total measured arc 8 as described above. Particular difficulties also occur for the intensities at the boundaries between subsequent parts of the arc.

SUMMARY OF THE INVENTION

It is an object of the present invention to avoid the disadvantages of the prior art described above which result from the step-wise progression of detector 6, and especially the matter of precise settings on the one hand and rest time on the other hand. The smaller the rest time is made, (i.e., the time between the step-wise movement) the greater are the problems that result in connection with the attainment of a sufficiently precise setting each time.

In an X-ray diffractometer according to the invention, a computer means is provided for plotting of the intensity diagram of a positional dispersion of the diffracted beam for a given angular position of the detector along the arc. The computer means includes means for continuously computing an angular position of the continuously moving detector. The continuous computing means includes an impulse provider connected to the drive control of a drive means for moving the detector. This impulse provider reduces the number of impulses from the control device. An adder means is also provided having a first input connected to the impulse provider and a second input connected to an analog-digital converter which converts analog position signals from a position sensitive element within the detector to digital information. An output of the adder connects to a multi-channel analyzer. The adder sums all the impulses which have arrived up to a given moment from the impulse provider at the first input with this sum representing an angular position of the detector at any given moment. The adder also provides a sum of the impulses at the second input representing and derived from the detector position signals. The adder then adds together the angular position sum and the detector position signal sum to produce a composite sum which is a continually changing indication of the precise angular position of X-rays striking the detector at a given position on the detector. This composite sum is continually updated as the detector moves along the arc and as diffracted X-rays strike the position sensitive element on the detector at various points.

With the invention, the detector 6 is moved substantially continually on the measured arc 8. Step-wise movement is not noticeable for the process of measuring since the steps are small and carried out continuously. The invention further supplements the already known computer electronics for plotting the powder diagram in the diffractometer.

DESCRIPTION OF THE PREFERRED EMBODIMENTS

Figure 1:
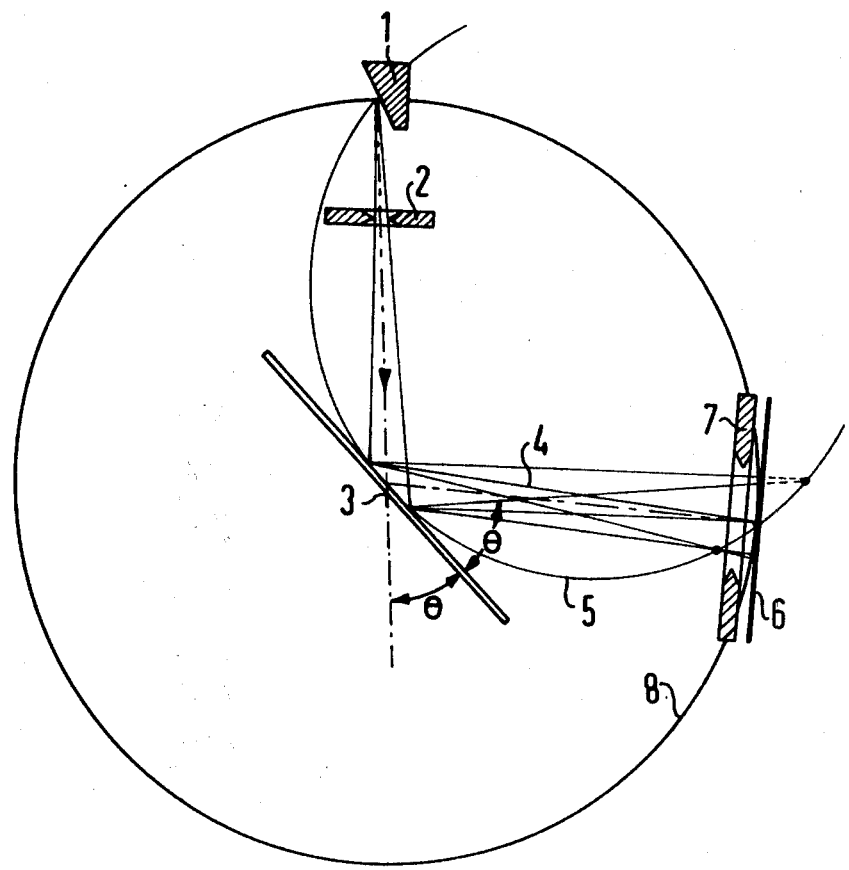
FIG. 1 is a cross-sectional view of a known diffractometer arrangement employing a goniometer for angle measurement of diffracted X-rays.
Figure 2:
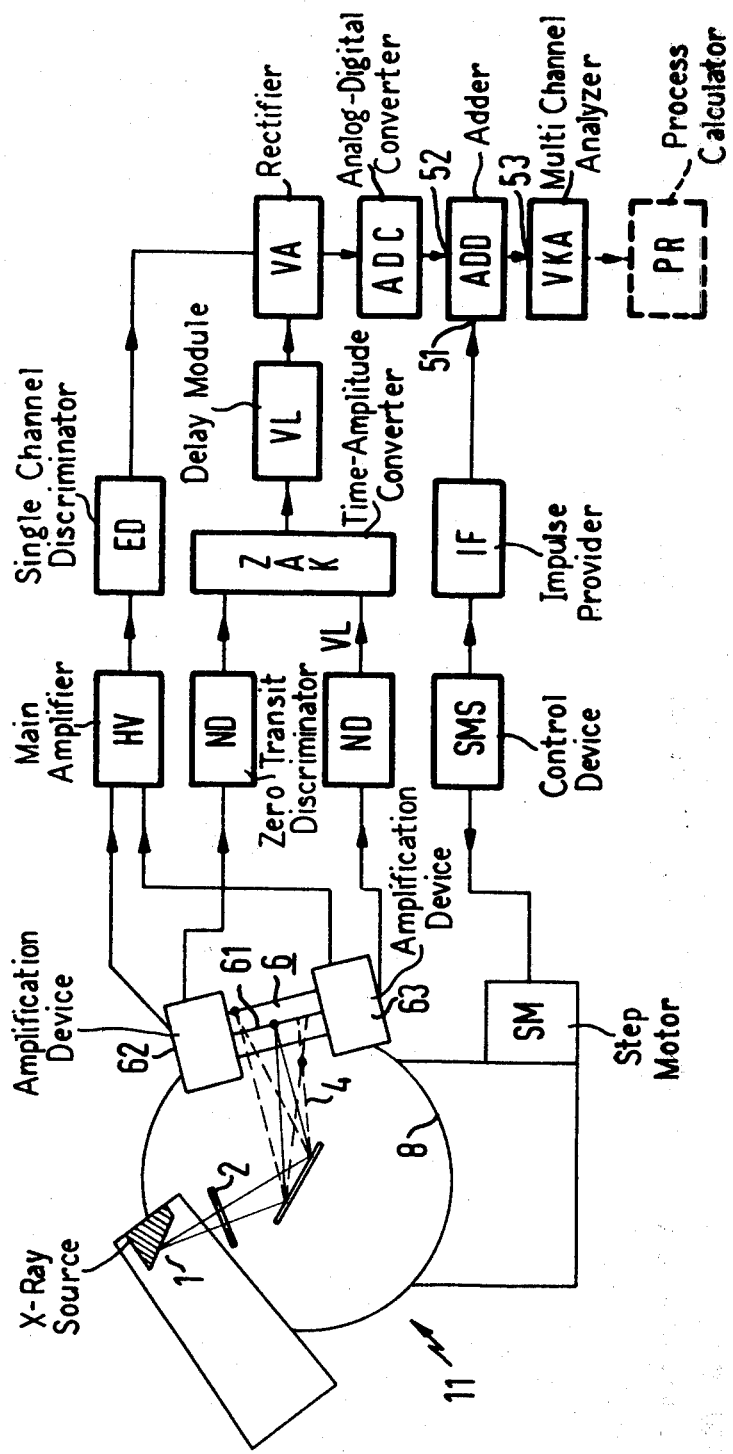
FIG. 2 is a block diagram of a diffractometer system employing the goniometer of FIG. 1 in conjunction with a computing system for producing an intensity diagram.

FIG. 2 shows an X-ray powder diffractometer according to the invention with known computer electronics and, according to the invention, additional electronic equipment used in the invention. 11 denotes the goniometer of the diffractometer. The specific circuit blocks in FIG. 2 are already known to one skilled in the art and commercially available models for each circuit are listed thereafter. 1 denotes the source for the monochromatic X-ray beam. The measured arc is again denoted by 8, along which movable detector 6 already discussed. This detector 6 has, as is known per se, a behavior which is sensitive to position resulting from the fact that a counting wire 61 employed with the detector 6 is prepared such that on both ends of the counting wire there are connected amplification devices 62, 63 which permit determination of the precise location of elementary phenomenon resulting from differing propagation and/or differing impulse slopes. These conclusions or results which occur as electrical signals are fed into a circuit used with powder diffractometers as is already known. This circuit has among other components a delay module VL as an output, an analog digital converter ADC, and a multichannel analyzer VKA. In addition, a process calculator PR can be connected to the analyzer VKA. Such known computer electronics does not, however, have a rectifier VA, an adder ADD, or an impulse provider IF as shown in FIG. 2. In the prior known circuits the following components are also employed: A main amplifier HV; a zero transit discrimnator ND, a one channel discriminator ED; and a time amplitude converter ZAK. The step motor SM is regulated by a control device SMS. It is to be noted that the step motor of the invention performs steps having a dimension of $1/1000°$ of the angle, i.e., basically offers continuous operation. This step motor is controllable via the control device SMS by means of controlling impulses. The known components used in the computer electronics are suited for plotting the X-ray diagram for a single detector position at each angle. According to the invention, however, detector 6 is moved continuously on the measured arc 8, an adder ADD is additionally provided, and wherein continuous computing occurs.

The adder has two inputs 51 and 52 and an output 53. Impulses which experience a numerical reduction in speed in the yet-to-be-described impulse provider IF are conveyed to input 51 from the control device SMS. These impulses which arrive at output 51 are continuously summed up in the adder ADD. The resulting sum of the previously occurring impulses at any given moment is a measure of the angular position $\theta$ of detector 6 in the goniometer 11. From the analog-digital converter, impulses arrive at input 52 of the adder, such impulses representing a digital signal corresponding to the input signal of this converter. Unlike the known computer systems, there is now employed an adder ADD for summing the number of up to the moment input impulses at input 51 and the digital impulses at input 52. These digital impulses at input 52 correspond, as in the known systems, to the positions of the elementary phenomenon in detector 6. Accordingly, the number of impulses which enter at input 52 for an elementary phenomenon in detector 6 indicates at which point along the counting wire of detector 6 this elementary phenomenon has occurred. The preceding can also be described in the following manner. The total number of ingoing impulses at input 51 indicates the momentary total progression angle $\theta$ of detector 6 on the measured arc 8, beginning at a zero position. The digital address which arrives from the analog digital converter at input 52 as momentarily determined at the same point in time indicates a differential angle variance which results from the fact that the length of the counting wire 61 of the detector 6 covers an angular sector in the goniometer and the elementary phenomenon occurs at a place along this wire with a positive or negative differential angle varian $\Delta\theta$. The sum of impulses of inputs 51 and 52 which occur at the output 53 of the adder indicate therefore the exact angular position $\theta + \Delta\theta$ of the elementary phenomenon on the counting wire in the goniometer 11. The continuing drive of the detector 6 is taken into consideration by means of the constantly rising number of impulses at input 51. the impulses of input 52 indicate a correction of the angle, so to speak, so that a signal is produced at the multichannel analyzer VKA which translates the elementary phenomenon in the detector without angle error in the goniometer. The signal at the output 53 or at the input of the multichannel analyzer VKA always arrives at the right memory address even though the detector is continuously being moved forward. As is known, the interrogation of the multichannel analyzer is achieved each time after a full sweep of detector 6 over the measured arc 8.

In the invention it is important that a precise rectification of the impulses which occur at inputs 51 and 52 is provided. From the impulse provider IF a reduction of the number of impulses from the control device has been provided for the reason that this control device has an awkwardly high frequency. For example, a reduction is achieved such that for one sweep of the measured arc 8 a total of 4000 impulses occur from the impulse transmitter at input 51. This is suited to a multichannel analyzer with 4096 channels.

A rectifier VA now serves to standardize the impulses of the elementary phenomenon with the angle measurement of input 51 which is given through the number of impulses. This should be understood as follows. For 1° of angular progression along the measured arc 8, 25 impulses arrive at input 51, for example. The rectifier VA is set particularly by hand such that now 25 impulses (for an elementary phenomenon) also occur at the output of the analog-digital converter for the $\theta = 1°$ variance of angle at the counting wire. According to the invention, since the impulse frequencies which are to be processed from the electronic circuits can be relatively high, a relatively rapid sweep of the angle by detector 6 on the measured arc 8 can be carried out in the diffractometer. For example, 30° to 50° on the measured arc 8 can be run through within one minute. For the total measured arc, an expenditure of time of less than 5 minutes is required. (Even 200°/min are possible)

The following commercially available components are suitable for the circuit blocks illustrated in FIG. 2;

HV - Siemens C 72249-A310-A1
ED = Siemens C 72249-A310-A1
SMS = Siemens C 72298-A170-B4
ND = Canberra Nucl. Electr. Timing SCA 835
ZAK = Canberra Nucl. Electr. Time Analyzer 1443
VL = Canberra Nucl. Electr. Time Analyzer 1443
ADC = Canberra Nucl. Electr. Mod. 8040 10
VKA = Canberra nucl. Electr. Mod. 8/00/04/4K ADD = Canberra Nucl. Electr. Svudergerat 8000 D
IF = Canberra Nucl. Electr. Svudergerat 8000 D Although various minor modifications may be suggested by those versed in the art, it should be understood that I wish to embody within the scope of the patent warranted hereon, all such embodiments as reasonably and properly come within the scope of my contribution to the art.

I claim as my invention:

1. An X-ray powder diffractometer for diffraction analysis by generation of an intensity diagram produced by X-rays diffracted on a sample comprising:
   (a) a source for monochromatic X-ray beaming;
   (b) a detector with position-sensitive detecting means for producing position signals in response to detected X-rays at a given position on the detector;
   (c) a drive means and connected drive control means for controllably continuously moving the detector along an arc, said drive control means producing impulses related to angular movement of the detector by the drive means;
   (d) computer means for plotting of the intensity diagram of a positional dispersion of the diffracted beam for a given angular position of the detector along the arc, said computer means including
      (i) processing means for processing the position signals from the detector,
      (ii) an analog-digital converter connected to the processing means,
      (iii) means for continuous computing of angular position of the continuously moving detector including
         (A) an impulse provider means connected to the drive control means for reducing the number of impulses from the control device, and
         (B) adder means having a first input connected to the impulse provider means, a second input connected to the analog-digital converter, and an output connected to a multichannel analyzer, said adder means summing all impulses which have arrived up to a given moment from the impulse provider at the first input, the sum representing an angular position of the detector at the given moment, said adder means producing a sum of the impulses at the second input representing and derived from the detector position signals, and said adder means adding together the angular position sum and the detector position signal sum to produce a composite sum indicating angular position of X-rays striking the detector at said given position on the detector, said angular position sum, detector position signal sum, and composite sum being periodically repeated to provide a continuous indication of angular position of detected dispersed X-rays.

2. A diffractometer as claimed in claim 1, characterized in that a rectifier means is provided to adapt the scale of the angle, said rectifier means being connected with an impulse input at the output of the processing means and with its output at the input of the analog digital converter.

3. A diffractometer as claimed in claim 1, characterized in that said processing means includes a single channel discriminator connected to a gate input of the rectifier means and a delay module connected to the input of the rectifier means.

4. An X-ray powder diffractometer for diffraction analysis by generation of an intensity diagram produced by X-rays dispersed by a sample, comprising:
   (a) a detector means having a position sensitive element means for producing position signals corresponding to the position at which detected X-rays strike the element means;
   (b) step motor means for continuously advancing the detector means during measurement along an arc over a desired angle;
   (c) control means connected to the step motor means for producing impulses corresponding to steps of the step motor;
   (d) analog-digital converting means for converting the detector means position signals to corresponding impulses; and
   (e) adding means for periodically summing the impulses corresponding to the detector position signals arriving at the moment and for maintaining a sum of all impulses which have arrived from the step motor control means at any given moment, the adding means adding the two sums together periodically to provide a composite sum corresponding to an angle at which a dispersed X-ray is received by the detector along the arc.

* * * * *